US008348879B2

(12) United States Patent
Gao et al.

(10) Patent No.: US 8,348,879 B2
(45) Date of Patent: *Jan. 8, 2013

(54) SURGICAL SYSTEM HAVING A CASSETTE WITH AN ACOUSTIC AIR REFLECTOR

(75) Inventors: Shawn X. Gao, Irvine, CA (US); Nader Nazarifar, Laguna Nigel, CA (US); Cornelis J. Drost, Ithaca, NY (US); Yuri M. Shkarlet, Pompano Beach, FL (US)

(73) Assignee: Novartis AG, Basel (CH)

( * ) Notice: Subject to any disclaimer, the term of this patent is extended or adjusted under 35 U.S.C. 154(b) by 1181 days.

This patent is subject to a terminal disclaimer.

(21) Appl. No.: 11/510,903

(22) Filed: Aug. 28, 2006

(65) Prior Publication Data

US 2008/0097284 A1    Apr. 24, 2008

(51) Int. Cl.
*A61N 1/30*    (2006.01)
*G01F 1/66*    (2006.01)
(52) U.S. Cl. .................... 604/19; 73/861.25
(58) Field of Classification Search ............ 604/30–34, 604/27, 118, 246, 131; 417/477.2; 73/861.25, 73/861.26
See application file for complete search history.

(56) References Cited

U.S. PATENT DOCUMENTS

| 4,395,258 A | 7/1983 | Wang et al. |
| 4,479,761 A | 10/1984 | Bilstad et al. |
| 4,493,695 A | 1/1985 | Cook |
| 4,592,741 A | 6/1986 | Vincent |
| 4,627,833 A | 12/1986 | Cook |
| 4,713,051 A | 12/1987 | Steppe et al. |
| 4,758,238 A | 7/1988 | Sundblom et al. |
| 4,773,897 A | 9/1988 | Scheller et al. |
| 4,790,816 A | 12/1988 | Sundblom et al. |
| 4,798,850 A | 1/1989 | Brown |
| 4,842,584 A * | 6/1989 | Pastrone ................ 604/505 |
| 5,117,698 A | 6/1992 | Baumoel |
| 5,267,956 A | 12/1993 | Beuchat |
| 5,273,517 A * | 12/1993 | Barone et al. ........... 494/37 |
| 5,324,422 A * | 6/1994 | Colleran et al. ......... 210/85 |
| 5,342,422 A * | 8/1994 | Wimbock ................ 55/444 |
| 5,364,342 A | 11/1994 | Beuchat et al. |
| 5,463,906 A * | 11/1995 | Spani et al. ............. 73/861.27 |
| 5,514,102 A | 5/1996 | Winterer et al. |
| 5,526,699 A | 6/1996 | Dorr |
| 5,650,572 A | 7/1997 | Vontz |
| 5,697,910 A * | 12/1997 | Cole et al. ............... 604/153 |
| 5,746,241 A | 5/1998 | Stedman |
| 5,747,824 A | 5/1998 | Jung et al. |
| 6,098,466 A | 8/2000 | Shkarlet |
| 6,599,277 B2 | 7/2003 | Neubert |
| 6,634,237 B2 | 10/2003 | Neubert |
| 6,901,812 B2 | 6/2005 | Moscaritolo et al. |
| 7,034,937 B2 | 4/2006 | Crudge et al. |

FOREIGN PATENT DOCUMENTS

| EP | 1 435 511 | 7/2004 |
| WO | WO93/03334 | 2/1993 |
| WO | 2003/000026 A2 | 1/2003 |
| WO | WO 2004/008081 | 1/2004 |

\* cited by examiner

*Primary Examiner* — Nicholas Lucchesi
*Assistant Examiner* — Jenna Zhang

(57) ABSTRACT

A surgical cassette have a rigid fluid channel formed into a rigid plastic component or housing. The piezoelectric crystals of an ultrasonic flow meter are positioned on one side of the fluid channel. The side wall of the fluid channel opposite the piezoelectric crystals is exposed to fluid in the flow channel on its interior side and is exposed to ambient air on its exterior side. The interface between the wall and the air acts as an acoustic reflector for the operation of the ultrasonic flow meter.

1 Claim, 5 Drawing Sheets

SURGICAL SYSTEM HAVING A CASSETTE WITH AN ACOUSTIC AIR REFLECTOR

BACKGROUND OF THE INVENTION

The present invention relates to an ultrasonic flow sensor and more particularly to a surgical system and cassette having an ultrasonic flow sensor.

Conventional ophthalmic surgical instrument systems use vacuum to aspirate the surgical site and positive pressure to irrigate the site. Typically, a cassette is serially connected between the means used to generate pressure and the surgical instrument. The use of cassettes with surgical instruments to help manage irrigation and aspiration flows at a surgical site is well known. U.S. Pat. Nos. 4,493,695 and 4,627,833 (Cook), 4,395,258 (Wang, et al.), 4,713,051 (Steppe, et al.), 4,758,238 and 4,790,816 (Sundblom, et al.), 5,267,956 (Beuchat), 5,364,342 (Beuchat et al.), and 5,747,824 (Jung, et al.) all disclose ophthalmic surgical cassettes with or without tubes, and they are incorporated in their entirety by this reference. Aspiration fluid flow rate, pump speed, vacuum level, irrigation fluid pressure, and irrigation fluid flow rate are some of the parameters that require precise control during ophthalmic surgery.

Prior art devices have used pressure sensors in the aspiration and irrigation lines and calculate fluid flow rates based on the sensed pressure. In the past, measuring of fluid pressures in surgical cassettes has been very precise and as the resistance in the fluid paths is known, fluid flow rates can be calculated reliably from fluid pressure. Recent improvements in the reliability of ultrasonic flow sensors, however, have now made it possible to non-invasively measure fluid flow accurately.

For example, one ultrasonic flow sensor disclosed in U.S. Pat. No. 6,098,466 (Shkarlet) discloses a flow sensor capable of accurately measuring fluid flow in vessels or tubes having decreased sensitivity to flow distribution non-uniformities and decreased overall size by employing multiple angled reflector surfaces which cause incident ultrasonic waves from one or more ultrasonic transducers to pass through the flow volume multiple times and in multiple directions without changing the planar orientation of the ultrasound waves. The wave paths resulting from the multiple reflections and multi-directional illumination of the flow volume decreases the probe's size and sensitivity to spatial distribution non-uniformities. The multiple angled reflector surfaces also permit the transmitting and receiving ultrasonic transducers to be placed close to one another, thereby reducing the overall probe size and making them particularly useful for incorporation in the relatively small fluid flow cassette used in ophthalmic surgery. In order for an ultrasonic flow sensor to work, the transducer must be acoustically coupled to the tubing in which the fluid is flowing so that any air located between the transducer and the tubing is removed. Prior art flow sensors generally use an acoustic gel, such as a high water content hydrogel material, to accomplish the acoustic coupling. When the acoustic coupling needs to be used in connection with a surgical cassette installed within a surgical console, sterility and cleanliness are of concern, making an acoustic gel less desirable than an acoustic coupling that is formed as part of the cassette or the console and that requires no gel.

One prior art device described in U.S. Pat. No. 6,901,812 (Moscaritolo, et al.) uses the interior wall of the flow channel being measured as the acoustic reflector. This device, however, requires very precise machining of the interior wall in order to function. Such precise machine is difficult and expensive, especially with the relatively small and intricate fluid passages used in a surgical cassette.

Accordingly, a need continues to exist for a simple, reliable and accurate acoustic reflector that can be used on or with a surgical cassette.

BRIEF DESCRIPTION OF THE INVENTION

The present invention improves upon the prior art by providing a surgical cassette having a rigid fluid channel formed into a rigid plastic component or housing. The piezoelectric crystals of an ultrasonic flow meter are positioned on one side of the fluid channel. The side wall of the fluid channel opposite the piezoelectric crystals is exposed to fluid in the flow channel on its interior side and is exposed to ambient air on its exterior side. The interface between the wall and the air acts as an acoustic reflector for the operation of the ultrasonic flow meter.

Accordingly, one objective of the present invention is to provide a surgical cassette having an acoustic reflector.

Another objective of the present invention is to provide a surgical cassette having an acoustic reflector that is formed as part of the cassette.

Yet another objective of the present invention is to provide a surgical cassette having an acoustic air reflector.

These and other advantages and objectives of the present invention will become apparent from the detailed description, drawings and claims that follow.

DETAILED DESCRIPTION OF THE PREFERRED EMBODIMENTS

Figure 1:
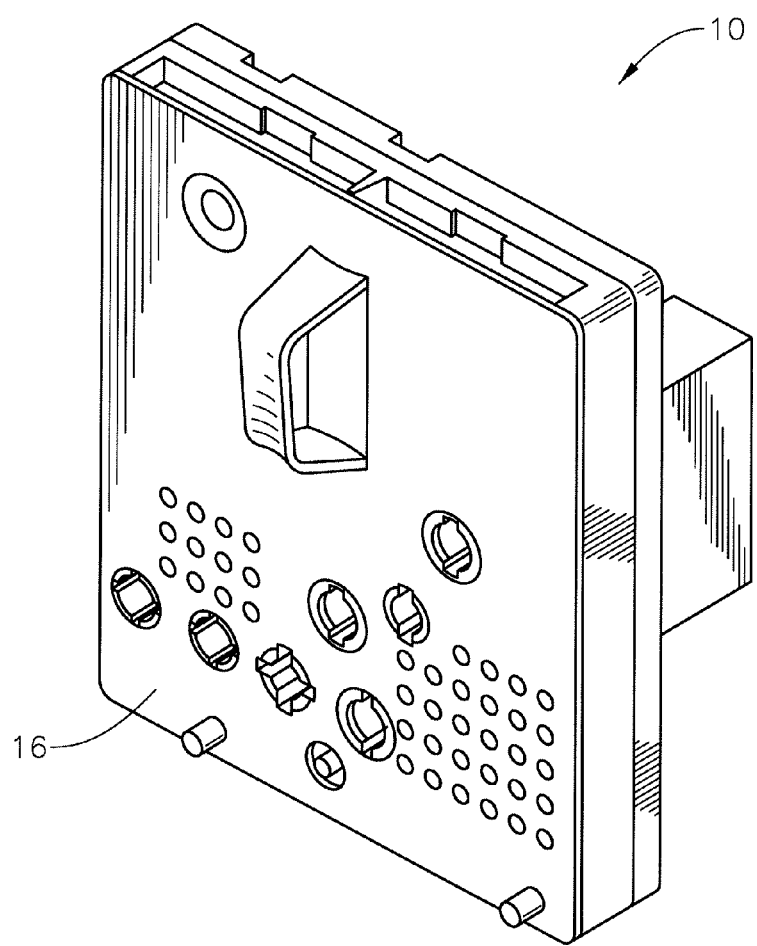
FIG. 1 is a front perspective view of the cassette of the present invention.
Figure 2:
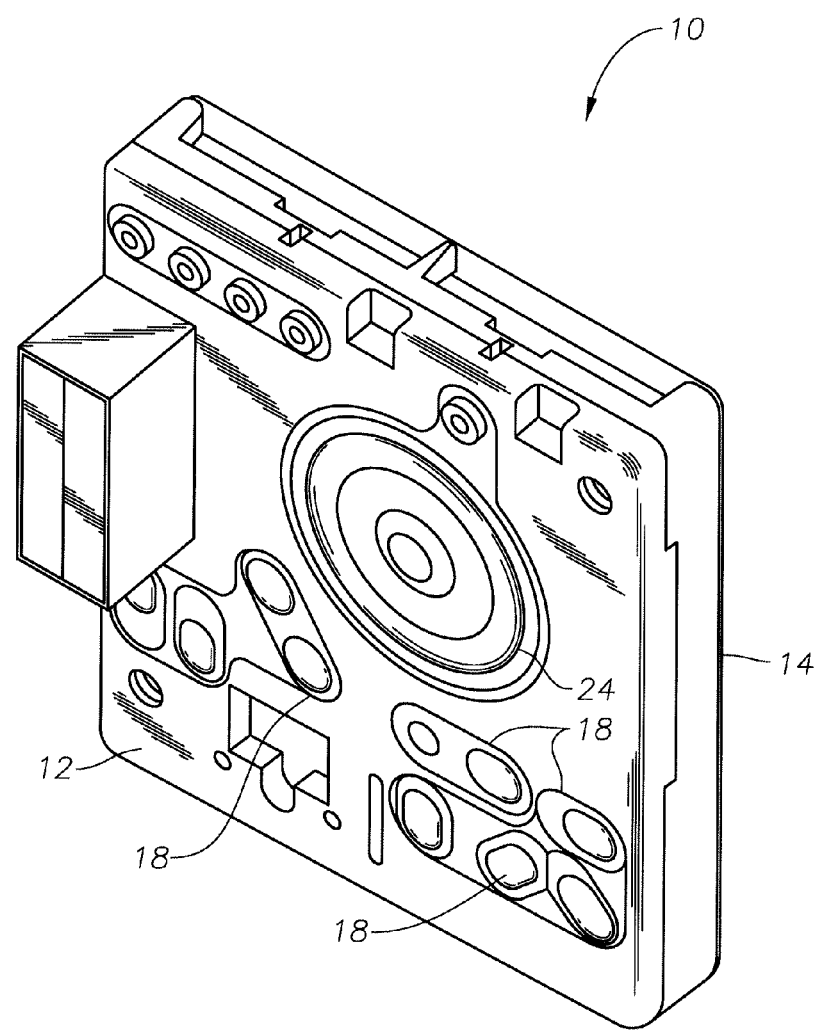
FIG. 2 is a rear perspective view of the cassette of the present invention.
Figure 3:
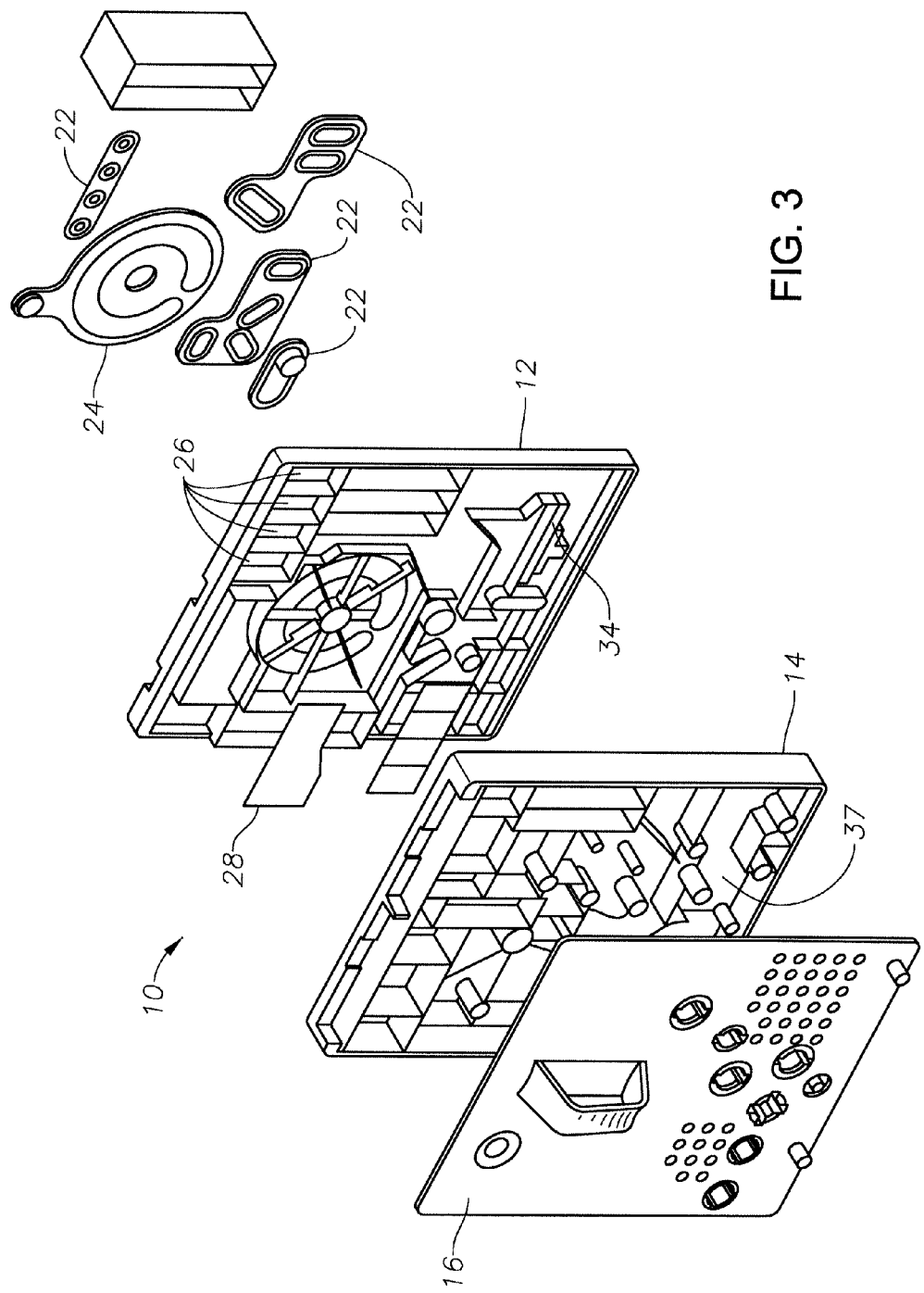
FIG. 3 is an exploded perspective view of the cassette of the present invention.
Figure 4:
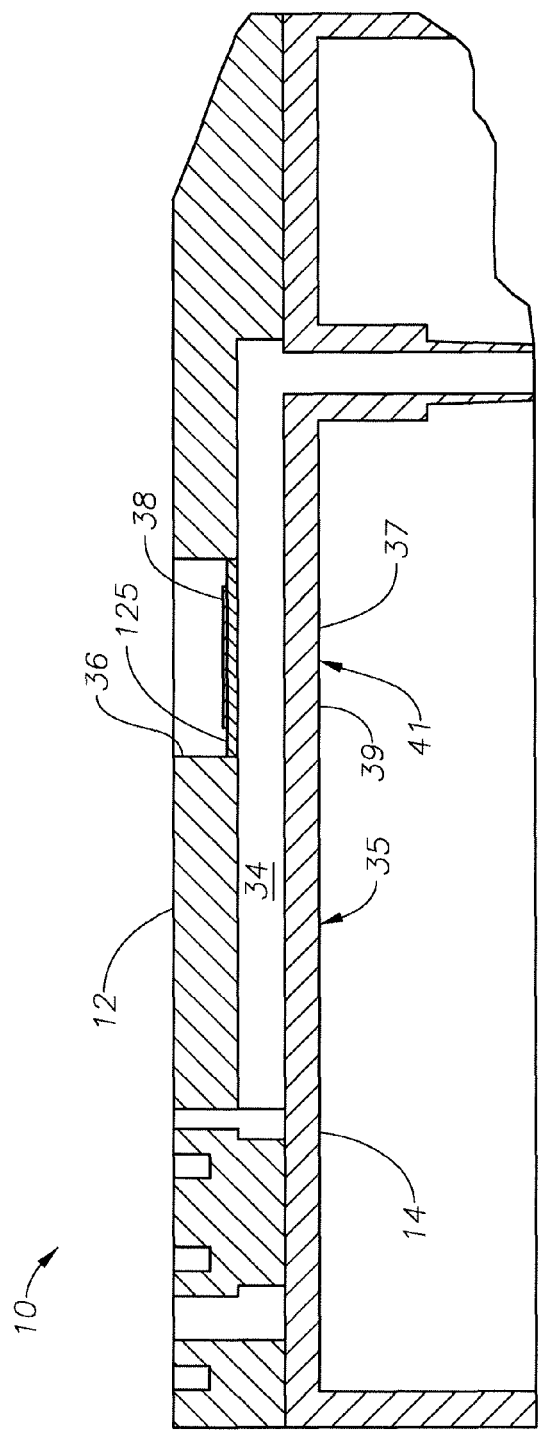
FIG. 4 is a partial cross-sectional view of the cassette of the present invention.
Figure 5:
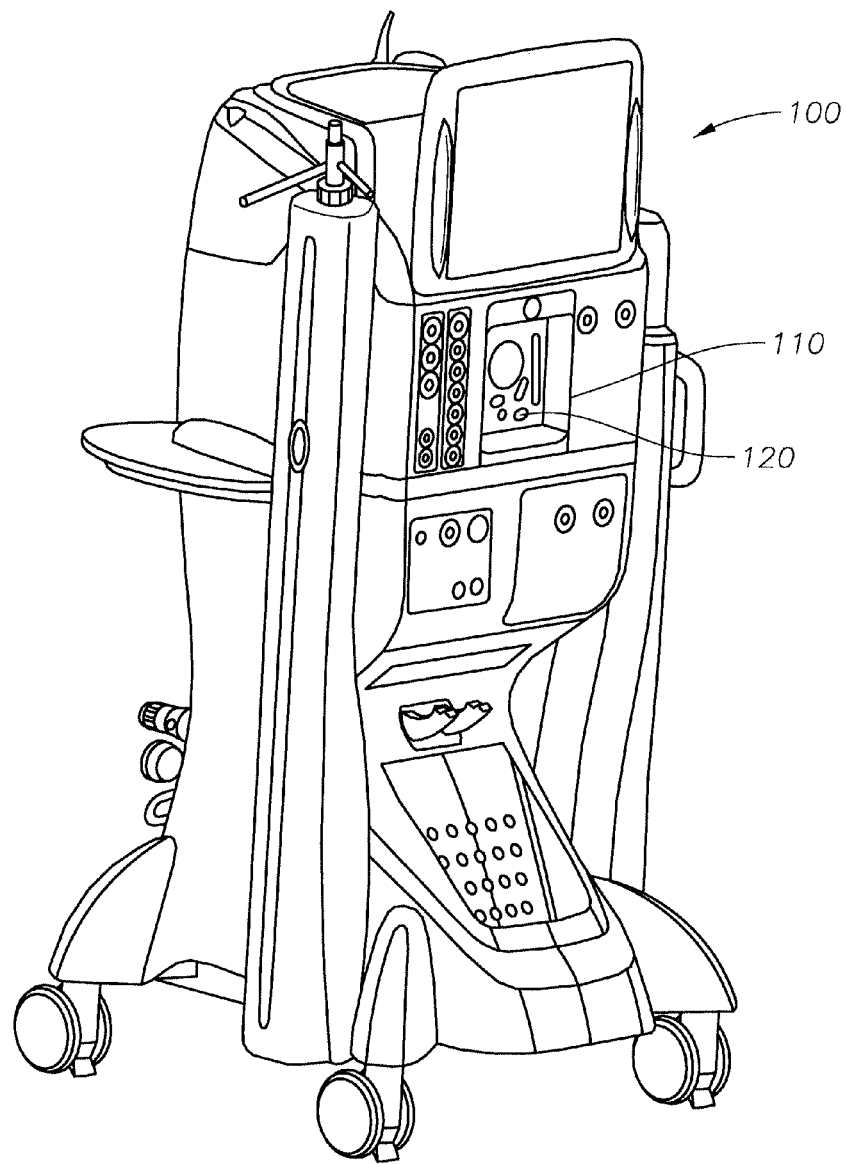
FIG. 5 is a front perspective view of a surgical console that may be used with the cassette of the present invention.

As best seen in FIGS. 1, 2 and 3, cassette 10 of the present invention generally included valve plate 12, body 14 and cover 16. Valve plate 12, body 14 and cover 16 may all be formed of a suitable, relatively rigid, thermoplastic. Valve plate 12 contains a plurality of openings 18 and pumping channel 20 that are sealed fluid tight by elastomers 22 and 24, forming a plurality of fluid paths. Ports 26 provide connectors between cassette 10 and surgical console 100 for the various irrigation and aspiration functions of cassette 10, such functions may requiring the use of filter 28. Forming part of fluid passage 34 is sidewall 35, which is formed as part of body 14. Portion 37 of sidewall 35 aligns with transmission window 125 in recess 36 when valve plate 12 is assembled onto body 14 in the manner shown in FIG. 3. Located within recess 36 on valve plate 12 is elastomeric acoustic coupler 38. When cassette 10 is installed in cassette receiving portion 110 of console 100, ultrasound transducer 120 presses against elastomeric acoustic coupler 38, providing an acoustic coupling between transducer 120 and fluid passage 34, thus allowing the use of ultrasound transducer 120 to measure the fluid flow rate in fluid passage 34 by projecting ultrasonic waves into fluid passage 34 and receiving the ultrasonic waves reflected off of wall/air interface 41 formed by exterior 39 of wall portion 37. Elastomeric acoustic coupler 38 preferably is formed by over molding an elastomeric material, such as a thermoplastic elastomer or silicone rubber within recess 36 of valve plate 12. Such a construction method eliminates the need for adhesives to attach elastomeric acoustic coupler 38 to valve plate 12 and ensures the removal of any air from between elastomeric acoustic coupler 38 and valve plate 12. The use of exterior wall/air interface 41 formed by portion exterior 39 of wall portion 37 eliminates the need for a separate acoustic reflector, with its required couplant material, thereby increasing reliability of the flow sensor and reducing the complexity and cost of cassette 10.

This description is given for purposes of illustration and explanation. It will be apparent to those skilled in the relevant art that modifications may be made to the invention as herein described without departing from its scope or spirit.

We claim:

1. A surgical cassette, comprising:
   a) a body made of a rigid plastic;
   b) a valve plate made of the rigid plastic, coupled to one side of the body, and having:
      a plurality of ports formed therein providing connections between the cassette and a surgical console;
      a recess disposed on the valve plate; and
      a transmission window disposed on a bottom surface of the recess;
   c) a plurality of elastomers attached to the valve plate, the elastomers forming a plurality of fluid paths;
   d) a cover made of the rigid plastic and coupled to an opposite side of the body;
   e) a fluid passage defined by the valve plate and the body and aligned with the transmission window; and
   f) an elastomeric acoustic coupler attached to the transmission window; wherein the body further comprises an ultrasound reflective surface aligned with the transmission window for reflecting an ultrasonic wave from an ultrasonic transducer of the surgical console, and the ultrasound reflective surface is an acoustic air reflector defined by a wall/air interface formed by an exterior of a rigid wall portion of the body.

* * * * *